United States Patent
Kawakita et al.

(10) Patent No.: US 10,267,756 B2
(45) Date of Patent: Apr. 23, 2019

(54) DRYNESS/WETNESS RESPONSIVE SENSOR HAVING FIRST AND SECOND WIRES SPACED 5 NM TO LESS THAN 20 μM APART

(71) Applicant: NATIONAL INSTITUTE FOR MATERIALS SCIENCE, Ibaraki (JP)

(72) Inventors: Jin Kawakita, Ibaraki (JP); Tadashi Shinohara, Ibaraki (JP); Toyohiro Chikyo, Ibaraki (JP); Toshihide Nabatame, Ibaraki (JP); Akihiko Ohi, Ibaraki (JP); Tomoko Ohki, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 0 days.

(21) Appl. No.: 15/327,103

(22) PCT Filed: Jul. 21, 2015

(86) PCT No.: PCT/JP2015/070692
§ 371 (c)(1),
(2) Date: Jan. 18, 2017

(87) PCT Pub. No.: WO2016/013544
PCT Pub. Date: Jan. 28, 2016

(65) Prior Publication Data
US 2017/0167995 A1 Jun. 15, 2017

(30) Foreign Application Priority Data
Jul. 23, 2014 (JP) ................................ 2014-149505

(51) Int. Cl.
*G01N 27/04* (2006.01)
*G01N 17/04* (2006.01)
(Continued)

(52) U.S. Cl.
CPC .......... *G01N 27/048* (2013.01); *G01N 17/04* (2013.01); *G01N 27/045* (2013.01);
(Continued)

(58) Field of Classification Search
CPC .... G01N 27/045; G01N 27/048; G01N 17/04; G01N 27/26; G01N 27/30
See application file for complete search history.

(56) References Cited

U.S. PATENT DOCUMENTS 3,540,278 A * 11/1970 Badertscher ......... G01N 27/121
73/335.02
4,515,653 A * 5/1985 Furubayashi ........ G01N 27/126
204/192.32
(Continued)

FOREIGN PATENT DOCUMENTS

DE 3911812 A1 * 10/1990 ........... G01N 27/121
EP 0584557 A1 * 3/1994 ........... G01N 27/121
(Continued)

OTHER PUBLICATIONS

International Search Report dated Oct. 6, 2015 in International Application No. PCT/JP2015/070692.
(Continued)

*Primary Examiner* — Jay Patidar
(74) *Attorney, Agent, or Firm* — Wenderoth, Lind & Ponack, L.L.P.

(57) ABSTRACT

A dryness/wetness responsive sensor having decreased size, and improved sensitivity and responsiveness. The present invention comprises a thin wire of a first metal and a thin wire of a second metal, which is different from the first metal, wherein the thin wires run in juxtaposition with each other on an insulating substrate, and wherein the spacing between the first thin wire and the second thin wire is in the range of 5 nm or more and less than 20 μm.

19 Claims, 20 Drawing Sheets

(51) Int. Cl.
*G01N 27/12* (2006.01)
*G01N 27/22* (2006.01)
*G01N 17/00* (2006.01)

(52) U.S. Cl.
CPC ......... *G01N 27/121* (2013.01); *G01N 27/223* (2013.01); *G01N 17/00* (2013.01)

(56) References Cited

U.S. PATENT DOCUMENTS

| | | | | |
|---|---|---|---|---|
| 4,816,748 | A * | 3/1989 | Tazawa | G01N 27/121 324/667 |
| 5,027,077 | A * | 6/1991 | Yanagisawa | G01N 27/121 324/606 |
| 5,348,761 | A * | 9/1994 | Mitter | G01M 3/045 252/408.1 |
| 5,455,513 | A * | 10/1995 | Brown | G01N 27/023 324/445 |
| 5,650,062 | A * | 7/1997 | Ikeda | C12Q 1/001 204/403.1 |
| 5,801,539 | A * | 9/1998 | Schroder | B60S 1/0822 318/483 |
| 6,342,295 | B1 * | 1/2002 | Kobayashi | G01N 27/121 338/35 |
| 7,176,700 | B2 * | 2/2007 | Itakura | G01N 27/223 324/670 |
| 8,262,875 | B2 * | 9/2012 | Paulus | G01N 27/3276 204/406 |
| 2003/0002238 | A1 * | 1/2003 | Toyoda | G01N 27/225 361/302 |
| 2003/0179805 | A1 * | 9/2003 | Hamamoto | G01N 27/225 374/16 |
| 2003/0222656 | A1 * | 12/2003 | Phillips | G01N 27/02 324/605 |
| 2009/0322543 | A1 * | 12/2009 | Crnkovich | A61F 13/42 340/604 |
| 2011/0033764 | A1 * | 2/2011 | Wang | H01M 8/04253 429/430 |
| 2013/0318948 | A1 * | 12/2013 | Van Marion | F02D 41/1466 60/277 |
| 2015/0338363 | A1 * | 11/2015 | Dean, Jr. | G01N 27/02 73/170.26 |
| 2015/0346132 | A1 * | 12/2015 | Morosow | G01N 27/226 73/335.04 |
| 2016/0041113 | A1 * | 2/2016 | Pagani | G01N 27/223 324/694 |
| 2017/0356899 | A1 * | 12/2017 | Guder | G01N 27/121 |

FOREIGN PATENT DOCUMENTS

| | | | |
|---|---|---|---|
| EP | 0 801 303 | | 10/1997 |
| JP | 1-123140 | | 5/1989 |
| JP | 03018750 | A * | 1/1991 |
| JP | 04326053 | A * | 11/1992 |
| JP | 5-2007 | | 1/1993 |
| JP | 05119010 | A * | 5/1993 |
| JP | 05142182 | A * | 6/1993 |
| JP | 5-332964 | | 12/1993 |
| JP | 10-38843 | | 2/1998 |
| JP | 2001-349867 | | 12/2001 |
| JP | 2004-500855 | | 2/2004 |
| JP | 2006-70287 | | 3/2006 |
| JP | 2006-317263 | | 11/2006 |
| JP | 2007-303936 | | 11/2007 |
| JP | 2008-45876 | | 2/2008 |
| JP | 2008-96235 | | 4/2008 |
| JP | 2008-261691 | | 10/2008 |
| JP | 2011-85516 | | 4/2011 |
| JP | 2011-128091 | | 6/2011 |
| WO | WO 2008021462 A2 * | 2/2008 | ............ A61F 13/42 |

OTHER PUBLICATIONS

Office Action dated Oct. 3, 2017 in Japanese Application No. 2016-535935, with English translation.
Office Action dated May 1, 2018 in Japanese Application No. 2016-535935, with English translation.
Extended European Search Report dated Jan. 23, 2018 in European Application No. 15824136.4.

* cited by examiner

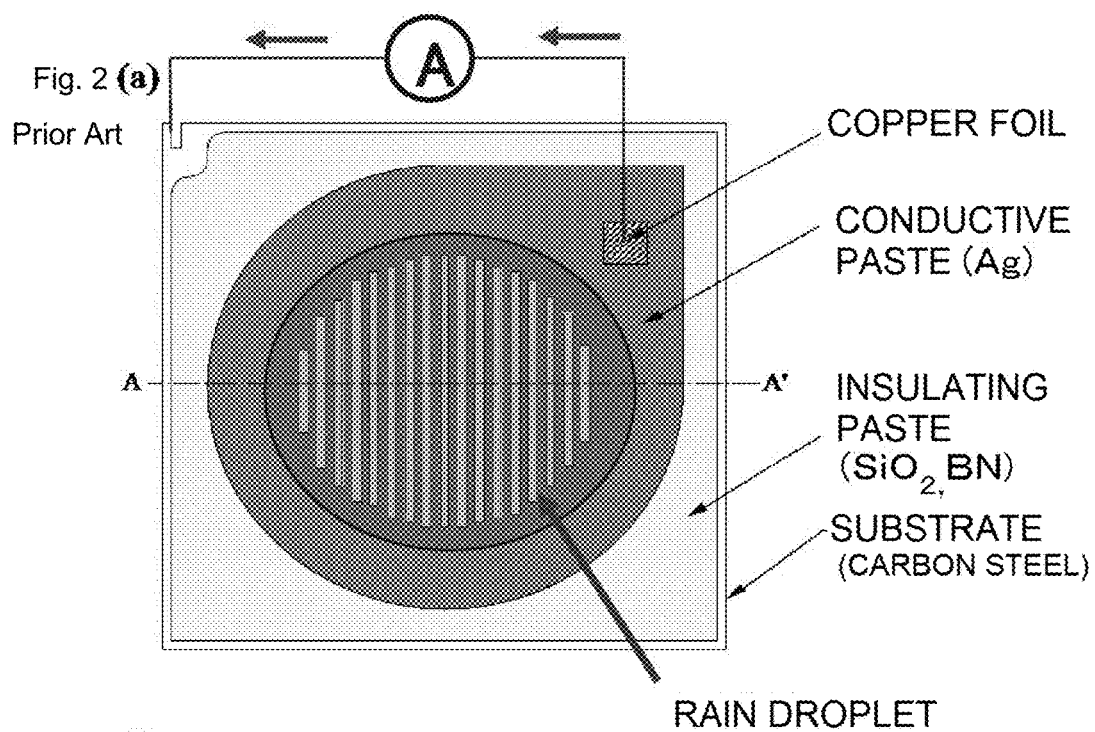
Fig. 2 (a) Prior Art
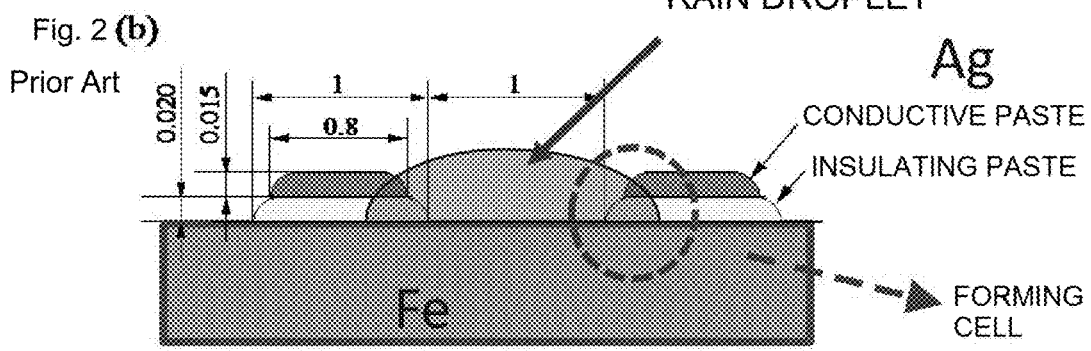
Fig. 2 (b) Prior Art

Fig. 4
Prior Art
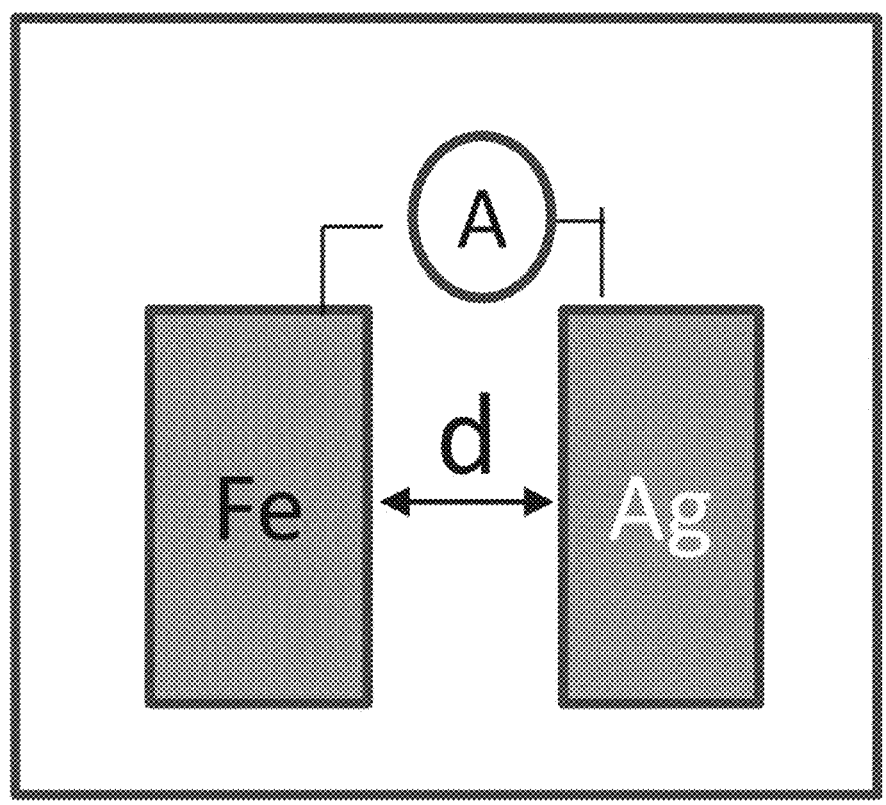
INTER-ELECTRODE
DISTANCE, d
DECREAS

Fig. 8B
(a) INTER-ELECTRODE DISTANCE 10μm
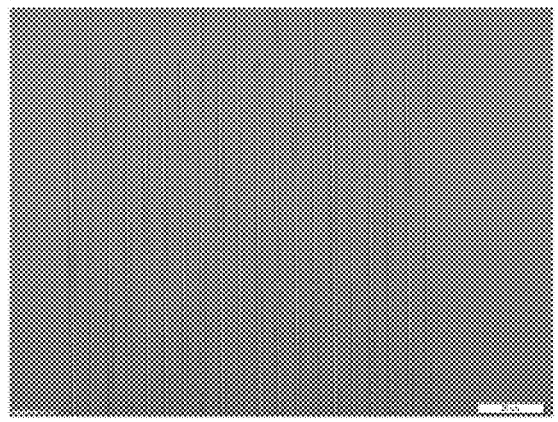
(b) INTER-ELECTRODE DISTANCE 1μm
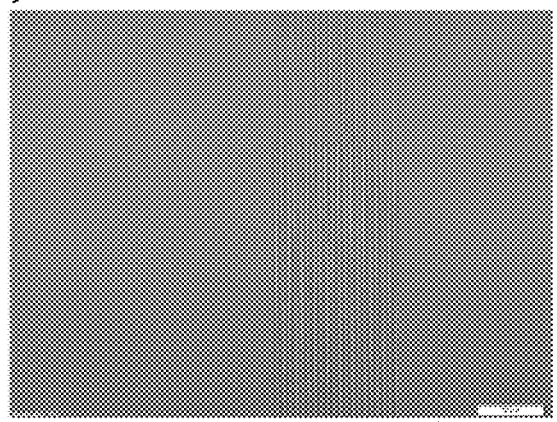
(c) INTER-ELECTRODE DISTANCE 0.5μm
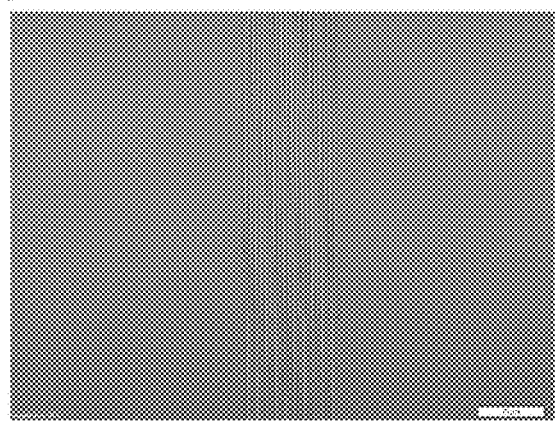

Fig. 9B
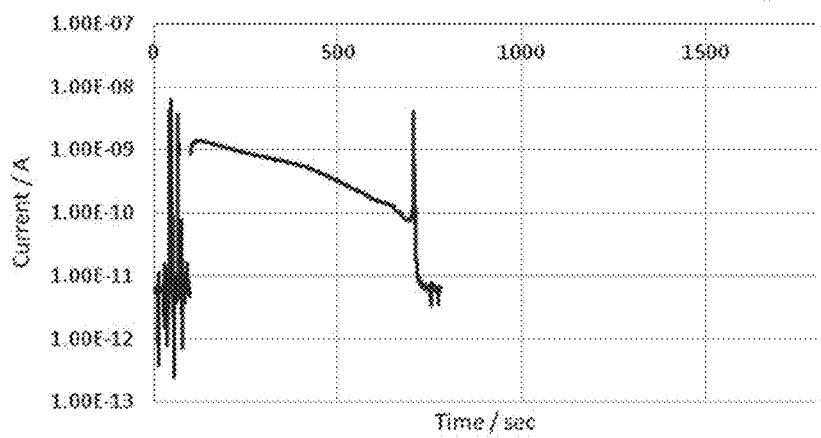
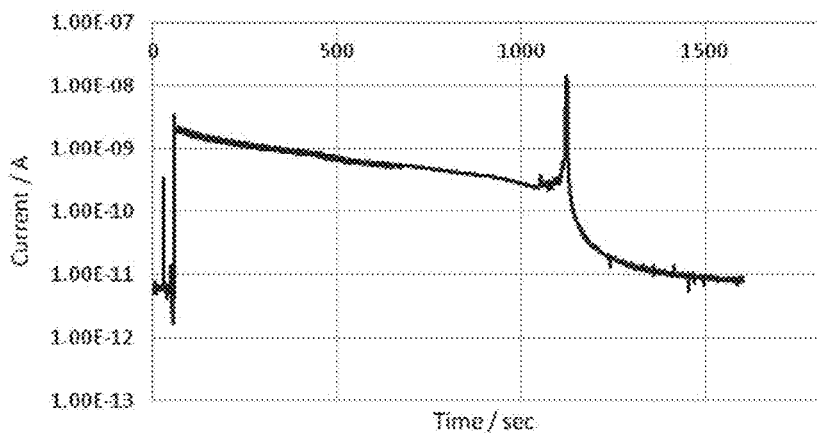
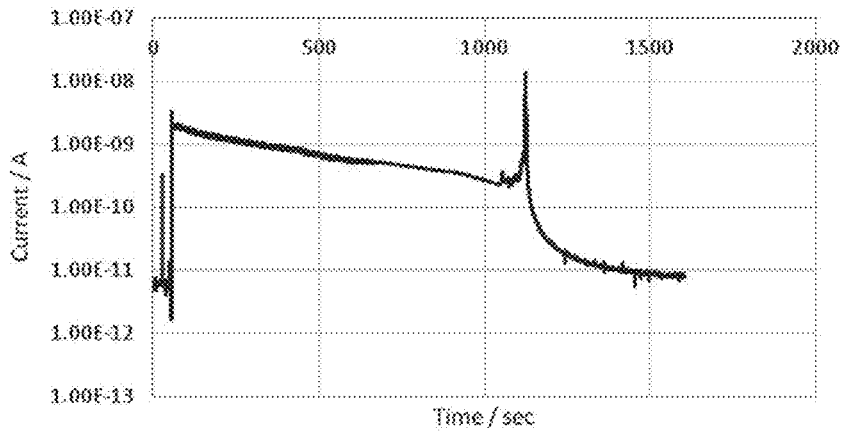

A-Slice

B-Slice

DRYNESS/WETNESS RESPONSIVE SENSOR HAVING FIRST AND SECOND WIRES SPACED 5 NM TO LESS THAN 20 µM APART

TECHNICAL FIELD

The present invention relates to a high-speed response/high-sensitivity dryness/wetness responsive sensor and, more particularly, to a dryness/wetness responsive sensor that has an appropriate structure for decreasing the size and increasing the sensitivity and realizes a high-speed response.

BACKGROUND ART

Conventionally, as dryness/wetness responsive sensors, humidity sensors are known which detect humidity based on a change in the electric resistance value (impedance) or electrostatic capacitance of a sensor element (dryness/wetness responsive part). In a humidity sensor of an electric resistance type, as a dryness/wetness responsive material of a sensor element, a polymer, ceramics, or the like is generally used, and since the material is low-cost and the structure is simple, a low cost can be achieved through mass production. However, if the humidity sensor of the electric resistance type gets wet with water, the sensor element will break down, and thus, the humidity sensor of the electric resistance type cannot be used under a condition in which dew condensation may occur. For this reason, the measurement humidity range is restricted to the range of 10 to 90% RH, and it is difficult to use the humidity sensor of the electric resistance type in a low humidity environment of 10% RH or less and in a high humidity environment of over 90% RH. In addition, the humidity sensor of the electric resistance type has a large aging variation, and, since it also has high temperature dependency in many cases, a temperature correction is required. Furthermore, the humidity sensor of the electric resistance type also has problems of large variation in precision (about ±5 to 15% RH) and a long response time (30 seconds to several minutes or even more).

In a humidity sensor of an electrostatic capacitance type, a polymer membrane is generally used as the dryness/wetness responsive material of the sensor element. Accordingly, the humidity sensor of the electrostatic capacitance type has a higher response speed (normally, about several seconds to ten seconds) and higher precision/reproducibility/reliability than the electric resistance type. Though its typical measurement humidity range is 0 to 100% RH, there are occasions when the sensor element is broken down under a dew condensation condition. In addition, the humidity sensor of the electrostatic capacitance type also has a problem of higher production cost than that of the humidity sensor of the electric resistance type.

A humidity sensor of both of the electric resistance type and the electrostatic capacitance type requires an external drive power supply for driving the sensor. In addition, a conventional humidity sensor cannot detect the size of water droplets attached to the surface of the sensor element due to its sensor structure or its detection principle.

Recently, a dryness/wetness responsive sensor based on galvanic action has been developed and used as a corrosion environment sensor that is used mainly for monitoring the corrosive environment of a construction.

In a bridge and other various constructions, since its steel members are often exposed to outside, the degree of corrosion of used steel members has great influence on the durability performance. The progress of corrosion of a steel member greatly varies according to not only the properties of the steel member itself but also use environments including the amount of a corrosive material and electrolytes contained in the atmosphere and rainwater, the amount of attached rainwater, and its wet time. Thus, in order to evaluate remaining lives of constructions of this type and appropriately maintain them by inspection, repair or the like, it is preferable to continuously evaluate the corrosion status for each of the constructions or, if necessary, for the respective portions of even one construction the corrosion environments of which are considered to be different from each other.

However, since it is difficult and takes a cost to perform an inspection of the degree of corrosion of a steel member itself configuring a structure on site, technique has been developed actually in which corrosion environment sensors are attached to respective places for evaluating their corrosion environments and the degree of corrosion of a steel member are estimated and predicted based on the evaluation results For example, as illustrated in FIG. 1, the degradation of the steel member of a bridge or the like was predicted by attaching a sensor of this type to the steel member and monitoring the corrosion environment at that place.

A representative example of the corrosion environment sensor is an atmospheric corrosion monitoring (ACM) sensor that detects a galvanic current flowing between metals of different types due to a contact therebetween via water. Refer to Non Patent Literatures 1 to 4 for its structure, method of evaluating measured data, and the like. However, since the size of the conventional galvanic sensor becomes larger for compensating for its low sensitivity, it has problems of inconvenience of the handling and high price.

SUMMARY OF INVENTION

Technical Problem

An object of the present invention is to improve the sensitivity and the responsiveness of a dryness/wetness responsive sensor with the operation principle of detection of a galvanic current, and in turn to decrease the size of the dryness/wetness responsive sensor.

Solution to Problem

According to one aspect of the present invention, there is provided a dryness/wetness responsive sensor comprising a thin wire of a first metal and a thin wire of a second metal, the second metal being different from the first metal, wherein the thin wire of the first metal and the thin wire of the second metal are disposed in juxtaposition with each other on an insulation substrate, and, wherein a spacing between the first thin wire and the second thin wire is in a range of 5 nm or more and less than 20 µm.

Here, a plurality of instances is provided for at least one of the thin wire of the first metal and the thin wire of the second metal, and the thin wire of the first metal and the thin wire of the second metal extend from mutually opposite sides toward the other sides so as to run in parallel.

Further, the thin wire of the first metal and the thin wire of the second metal may be arranged in a double spiral.

Further, the insulating substrates may be a silicon substrate with a silicon oxide film on its surface.

Further, the first metal may be selected from a group consisting of gold, platinum, silver, titanium, an alloy thereof, and carbon.

Further, the second metal may be selected from a group consisting of silver, copper, iron, zinc, nickel, cobalt, aluminum, tin, chromium, molybdenum, manganese, magnesium, and an alloy thereof.

Further, a meshed member covering an area in which the thin wire of the first metal and the thin wire of the second metal may be disposed in juxtaposition with each other.

Further, an insulating protection film covering an area in which the thin wire of the first metal and the thin wire of the second metal are disposed in juxtaposition with each other, wherein the insulting protection film has a groove-shaped opening that exposes at least a part of the thin wires.

Further, a groove-shape opening that exposes at least a part of a gap between the thin wire of the first metal and the thin wire of the second metal.

Further, an opening portion passing through between front and rear sides of the insulating substrate by removing at least a part of a position of the insulating substrate corresponding to a gap between the thin wire of the first metal and the thin wire of the second metal.

According to another aspect of the present invention, there is provided a dryness/wetness responsive sensor assembly for remote installation comprising an attachment member with an attachment portion at one end for attachment to an object to which any of the dryness/wetness responsive sensor described above is attached so as to allow the dryness/wetness responsive sensor to be remotely located.

According to yet another aspect of the present invention, there is provided a dryness/wetness responsive sensor system comprising a plurality of any of the dryness/wetness responsive sensors described above, where the dryness/wetness responsive sensor in the system in which a short circuit has occurred or which does not generate an output current is disconnected.

Here, the disconnection of the dryness/wetness responsive sensor may be performed by electrically disconnecting the dryness/wetness responsive sensor or not using an output of the dryness/wetness responsive sensor.

Advantageous Effects of Invention

According to the present invention, since a dryness/wetness responsive sensor of high sensitivity and high-speed responsiveness is provided that has a simple structure and needs no sensor driving power, the dryness/wetness responsive sensor can be reduced in size and price.

BRIEF DESCRIPTION OF DRAWINGS

FIGS. 2(a) and 2(b) are diagrams that illustrate the structure of a conventional corrosion environment sensor based on detection of a galvanic current. In the drawing, the dimension is in units of mm.

FIG. 4 is a conceptual diagram for illustrating a structure for improving the sensitivity of a corrosion environment sensor based on detection of a galvanic current.

FIG. 8B shows photographs illustrating the major portion of the dryness/wetness responsive sensor of the embodiment of the present invention for the cases where an electrode gap is 10 µm, 1 µm, and 0.5 µm.

FIG. 9B is a diagram for illustrating examples of the output of the dryness/wetness responsive sensor of the embodiment of the present invention for the cases where an inter-electrode distance were configured to be 10 µm, 1 µm, and 0.5 µm.

DESCRIPTION OF EMBODIMENTS

First, the structure of a conventional corrosion environment sensor using detection of a galvanic current disclosed in Non Patent Literature 3 will be described with reference to the drawings. FIG. 2(a) is a plan view of the corrosion environment sensor, and FIG. 2(b) is an enlarged diagram of a portion near a center portion of a cross-sectional view taken along A-A' represented in FIG. 2(a). In this corrosion environment sensor, for example, by coating a metallic substrate such as carbon steel with insulating paste (for example, $SiO_2$, BN, or the like), an insulating film formed using the insulating paste is formed on the substrate. By coating the insulating film with conductive paste, for example, a film of another metal such as silver is formed. A vertical-striped portion having a light color inside a tire-shaped area (sensor area) in FIG. 2(a) is a portion in which neither a film of a metal such as silver nor insulating paste is formed but a substrate of metal such as carbon steel is exposed. FIG. 2(b) illustrates a cross-sectional structure of this portion. In addition, a copper foil is attached to a portion deviating from the sensor area on the film of a metal such as silver so as to be set as an electrode. Also from the substrate formed using a metal such as copper steel, the other electrode is led out (an upper left corner in FIG. 2(a)). When this corrosion environment sensor is used, a current meter is connected between both the electrodes and measures a galvanic current.

Figure 1:
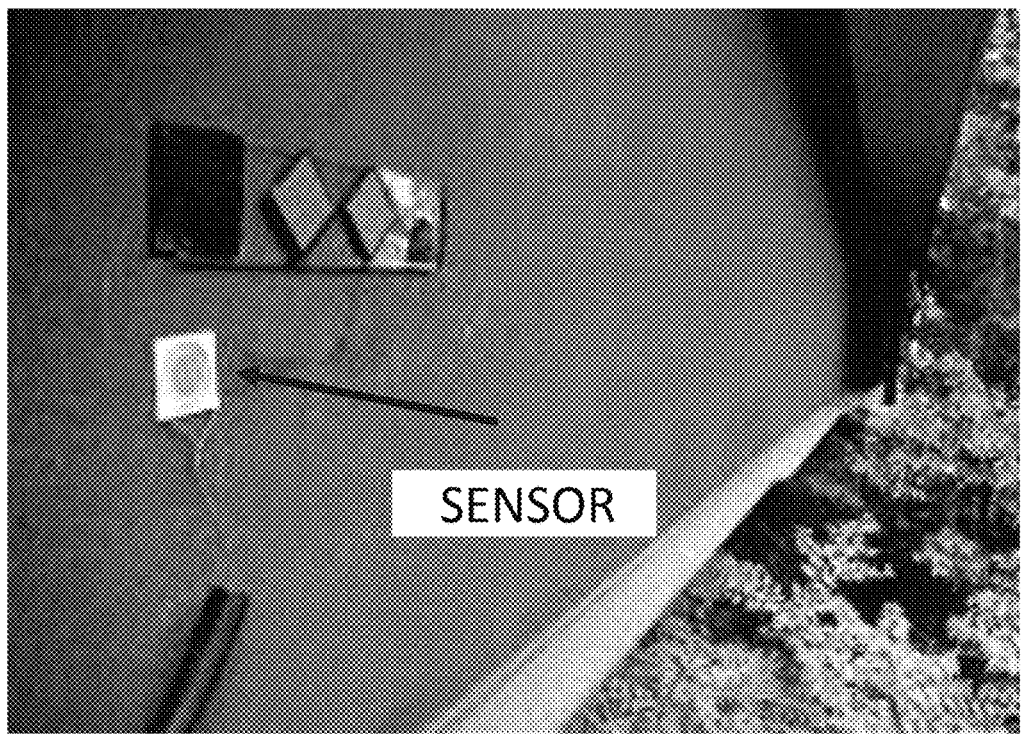
FIG. 1 is a photograph that illustrates an example of the use of a conventional corrosion environment sensor.
Figure 3:
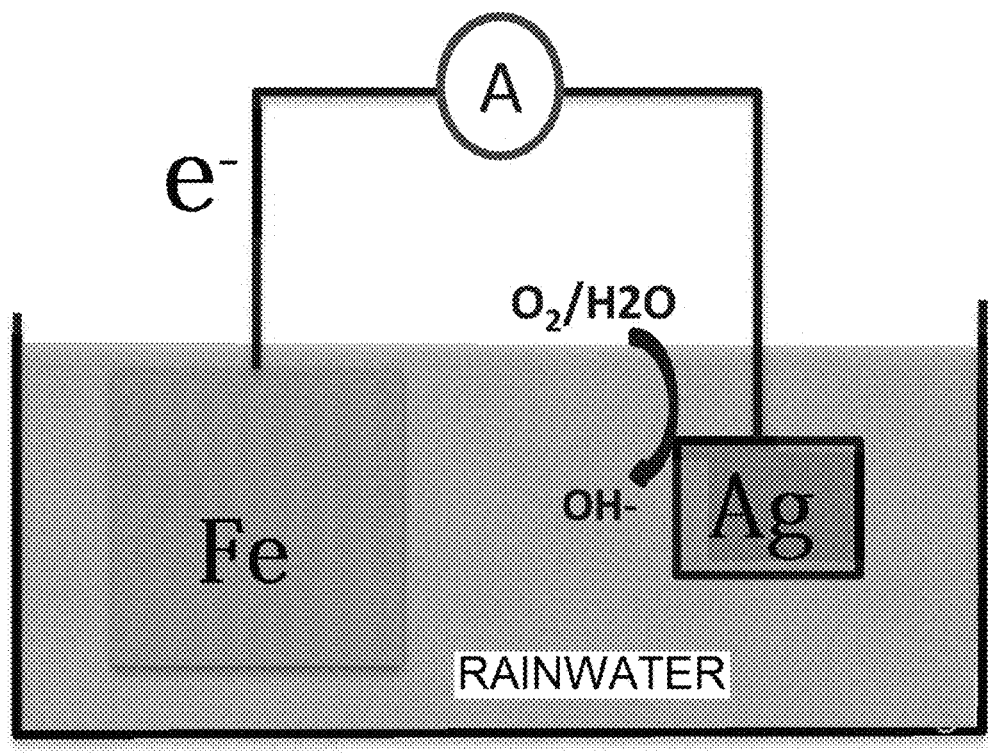
FIG. 3 is a conceptual diagram for illustrating the detection of a galvanic current.

In a case where this corrosion environment sensor is installed at an outdoor place, water (hereinafter, represented by rainwater) such as rainwater according to a rain fall is attached thereto. Naturally, the rainwater is not pure water but dissolves fine particles of salts floating in the atmosphere and gases (carbon dioxide, sulfur dioxide, nitrogen oxides, and the like) generating ions by being dissolved into water and, in addition, in the initial period of a rainfall, dissolves a solid substance attached to the surface of the corrosion environment sensor, and accordingly, rainwater attached to the sensor area becomes an electrolytic solution connecting metals (iron composing the substrate and silver on the insulating film) of different kinds. Accordingly, as illustrated in FIG. 2(b), a local cell formed by iron-rainwater-gold is formed along the periphery of the vertical-striped area of silver inside the sensor area. This local cell is conceptually illustrated in FIG. 3. Since the cell is formed in the sensor area in this way, in a case where the copper foil and the substrate are connected, a galvanic current according to the amount of the electrolyte in the rainwater flows. This current is measured by a current meter connected thereto. It is known that the magnitude of the galvanic current measured in this way has a strong correlation with corrosion according to a local cell formed on the surface of the steel member at the same place in accordance with to the same rainwater or the like, and accordingly, the progress of the corrosion can be evaluated by measuring the galvanic current.

Figure 5:
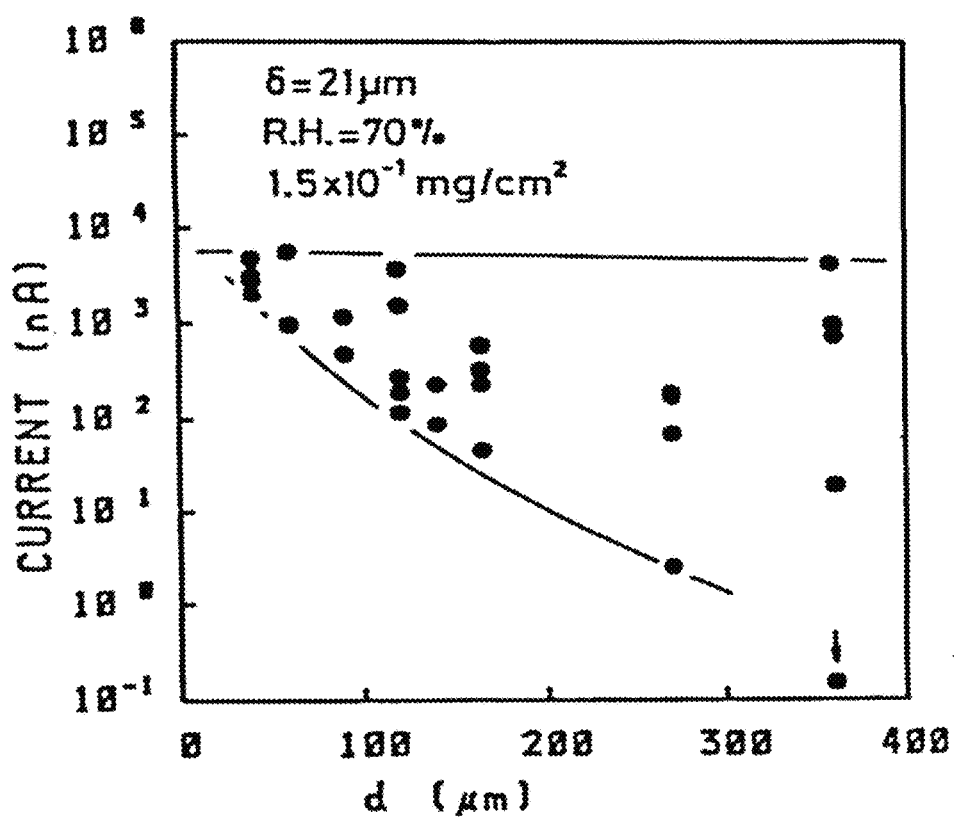
FIG. 5 is a graph for illustrating a lower limit of an electrode gap of a conventional corrosion environment sensor based on the detection of a galvanic current.

In a case where the size of the corrosion environment sensor is decreased, the degree of freedom in the attachment position increases, and the corrosion environment sensor is not conspicuous for the attachment thereof, and there is less restriction in the attachment position also from this point. In addition, generally, since the cost is lowered due to the decrease in size, implementation of multiple points of measurement positions can be easily performed. In the corrosion environment sensor using a galvanic current as illustrated in FIGS. 2(a) and 2(b), in principle, the sensitivity is improved in a case where a distance between two electrodes formed using different kinds of metals is decreased as illustrated in FIG. 4. However, in the corrosion environment sensor having the structure illustrated in FIGS. 2(a) and 2(b), there is a restriction in the decrease in the inter-electrode distance. FIG. 5 is quoted from Non Patent Literature 5 and is a graph in which a result of actually measuring a relation between an inter-electrode distance (d) of a corrosion environment sensor of this kind and a galvanic current at that time is plotted. As illustrated in this graph, while there is non-uniformity, in a case where the inter-electrode distance d is decreased, the galvanic current increases, in other words, the sensitivity is improved. However, the inter-electrode distance is decreased only up to about 20 μm. Accordingly, it is difficult to improve the sensitivity of the corrosion environment sensor using the galvanic current (more specifically, the improvement of the sensitivity of the sensor area per unit area).

The inventors of the present application have reviewed the cause of such restriction and a solution thereof and have found that there is a problem in a structure in which two electrodes (the substrate and the silver film) are vertically stacked through an insulating layer formed using the insulating paste in a conventional corrosion environment sensor of which the structure is illustrated in FIGS. 2(a) and 2(b). In other words, different from a device used under a protected environment such as a common electronic device, for the corrosion environment sensor having a natural premise of direct exposure for a considerably long period to an environment for which there is a risk for damaging the device such as outer air, various weather conditions, emission of sunlight, collisions with particles such as dusts, interferences from animals and plants, and the like, in order not to cause the function of a sensor to disappear due to a direct contact between the substrate of metal and a film of a different metal even in a case where there is a damage of some degree in the sensor area, there is a restriction on the decrease in the inter-electrode distance by thinning the insulating layer. In addition, the insulating layer is produced through coating using the insulating paste, and thus, in a case where the insulating layer is formed to be thin exceeding a certain limit, there are cases where an insulation defect occurs in the process of generating the sensor, and, even in a case where there is no problem at the time of the production, but the insulation is broken according to aging under a severe environment as described above. Furthermore, while the edge of the vertical-striped portion formed by the insulating layer and the metal layer is ideally erected vertically from the substrate, practically, as illustrated in FIG. 2(b), the edge may be easily inclined slightly, and thus, the inter-electrode distance increases also from this point.

Figure 13:
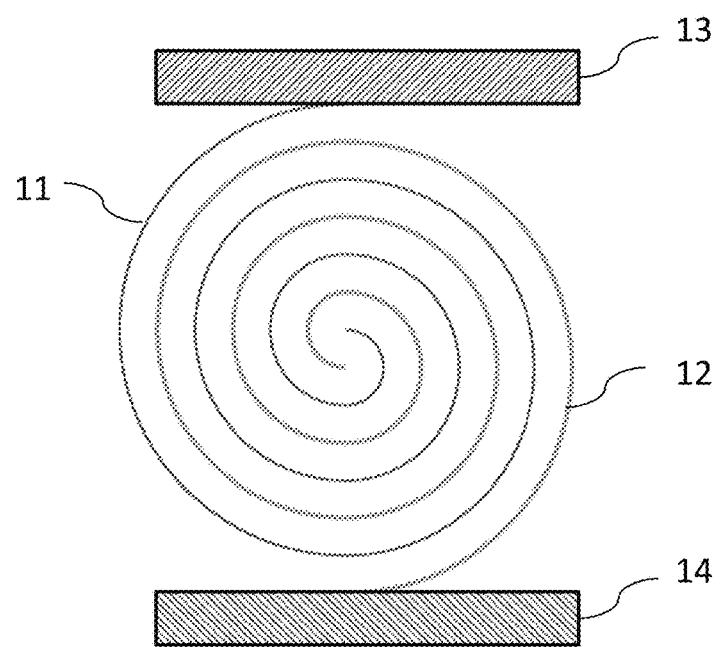
FIG. 13 is a diagram that illustrates an example of an electrode arrangement structure of a dryness/wetness responsive sensor.

For this reason, the inventors of the present application have conceived the idea in that the problem described above can be solved by employing a structure in which an electrode of a metal and an electrode of another metal are closely juxtaposed laterally on an insulating substrate instead of the conventional stacking structure of electrodes as illustrated in FIGS. 2(a) and 2(b). Describing this structure more specifically, portions of both electrodes facing each other are portions that mainly function as a cell that is locally generated, and thus, increasing a length of the portions of both the electrodes facing each other with approaching each other is more effective for an increase in the capacity of the cell, in other words, an increase in the galvanic current to be taken out than increasing the areas of such electrodes on the substrate. Accordingly, a structure in which such electrodes are thinned and arranged in parallel with each other over a long distance or the like may be employed. As a configuration for increasing a length (hereinafter, referred to as a parallel running distance) of approached portions between thin wires (electrodes) by arranging such thin wires in parallel with each other, for example, a comb structure or a double spirally-wound structure as illustrated in FIG. 13 may be employed. In addition, a structure itself for increasing a parallel running distance between two electrodes inside a predetermined plane area as possibly as can be is well known in the field of a semiconductor device and the like, and thus, such a structure may be employed as is necessary. In the present invention, "juxtaposing electrodes on a substrate" is not for specifying mutual directions of a plurality of electrodes placed on the substrate but represents that the electrodes are arranged on a same plane of the substrate with being separate from each other.

In this way, according to the present invention, by detecting liquid droplets present on the surface of a solid object in accordance with a phenomenon of dew condensation of water vapor contained in the air on the surface of the solid object or a phenomenon of adsorption of mist droplets onto the surface of the solid object based on a current that is based on the galvanic action between electrodes formed using different kinds of materials, a dryness/wetness responsive sensor capable of determining a dry/wet state at a high speed with high sensitivity is realized.

A dryness/wetness responsive sensor according to the present invention, compared to a conventional humidity sensor using a system measuring a dry/wet state through a process of absorbing moisture into a dryness/wetness responsive material, can directly detect liquid droplets attached to the surface of the sensor from the air and thus has high-speed responsiveness.

In addition, since there is dependency between an inter-electrode distance of the sensor and the size of liquid droplets, the dryness/wetness responsive sensor according to the present invention has high sensitivity that is completely different in nature from a conventional sensor. This point will be described below in detail.

Here, the insulating substrate has an insulating property of a degree not disturbing the measurement of a galvanic current flowing from the above-described cell formed thereon, and the material and the like thereof are not particularly limited as long as the insulating substrate has durability that is required under an assumed use environment. For example, in addition to a silicon substrate in which a coating film of silicon oxide used in the embodiment to be described hereinafter is formed, plastic, rubber, or any other various insulating materials can be used. In addition, as in the conventional technology described above, it should be noted that a substrate in a form having an insulating property seen from electrodes by forming insulating coating, insulating covering, or the like on a substrate main body that is a conductive body of a metal or the like also belongs the category of the "insulating substrate" in the present application.

By employing such a structure, the dryness/wetness responsive sensor according to the present invention can decrease the inter-electrode distance up to about 5 nm by using a technique of a semiconductor manufacturing process. While there is no particular upper limit of the inter-electrode distance, the upper limit may be 20 µm or less that is shorter than the inter-electrode distance according to the conventional technology described above. In this way, up to the attachment of a water droplet having an extremely small size and a fine water droplet that is in a state immediately before dew condensation, of which detection is difficult by using a sensor having an inter-electrode distance of 20 µm of more, which is manufactured using a conventional machine processing technology or a conventional printing technology, can be detected. Therefore, in the dryness/wetness responsive sensor according to the present invention, a correlation between a detection result acquired by the sensor and the progress status of corrosion is improved. Here, the inter-electrode distance may be a constant value in accordance with the use of the dryness/wetness responsive sensor, the installation environment, and the like, or a plurality of setting values may be combined.

As the inter-electrode distance is decreased, conductive fine particles such as metal powders present in the air, in the rainwater, and the like are attached between the electrodes, and accordingly, a possibility of forming a short circuit increases. Regarding this problem, by setting up a countermeasure as below, the occurrence of the problem can be prevented.

Figure 14A:
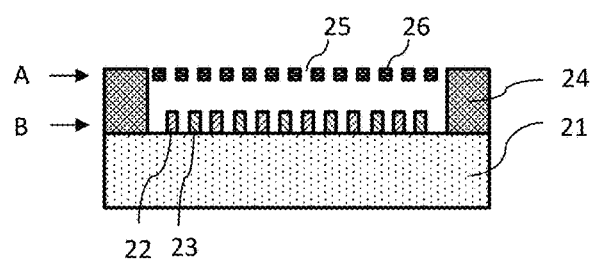
FIG. 14(a) is a schematic vertical cross section according to one embodiment of a dryness/wetness responsive sensor.
Figure 14B:
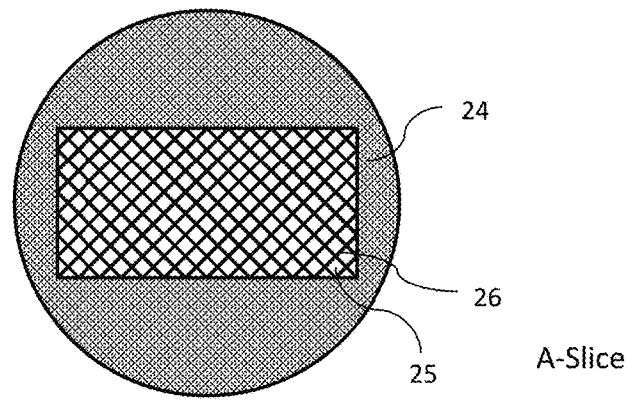
FIG. 14(b) is a slice cross section at a position A of the embodiment of FIG. 14(a)
Figure 14C:
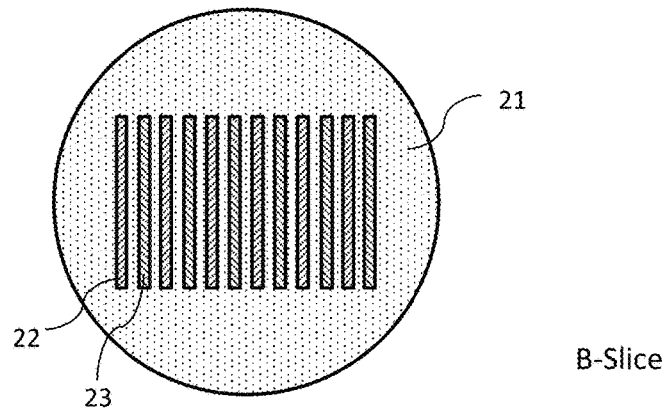
FIG. 14(c) is a slice cross section at a position B of the embodiment of FIG. 14(a).

(1) By arranging a meshed body on the front face of the electrodes, fine particles do not arrive at the electrodes. This embodiment is illustrated in FIGS. 14($a$), 14($b$) and 14($c$).

Figure 15:
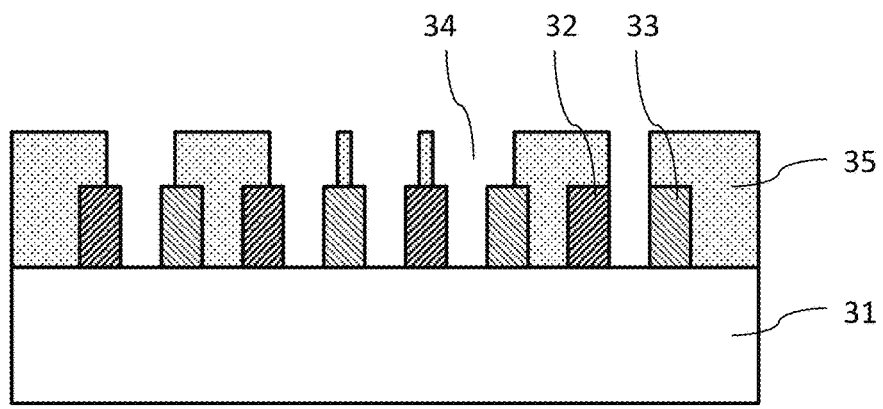
FIG. 15 is a schematic vertical cross section according to one embodiment of a dryness/wetness responsive sensor.

(2) An insulating protection film of a silicon oxide or the like is arranged on the front face of each electrode, and fine openings exposing at least a part of the thin wire of each electrode (in addition, at least a part of the gap between the thin wires, as needed) is formed in the insulating protection film. With this configuring, even when conductive fine particles are attached near the entrance of the fine opening portion of the insulating protection film, the fine openings prevent the particles from directly contacting the thin wire and causing a short circuit, since the thin wire of the electrode is positioned deep in the opening by the thickness of the insulating protection film. This embodiment is illustrated in FIG. 15.

(3) An approach from the aspect of the sensor system can be employed in which, for example, though the dryness/wetness responsive sensor itself having an ordinary structure according to the present invention is used, a plurality of such sensors are arranged closely to each other, and the sensor in which a short circuit between the cathode electrode and the anode electrode is detected or from which no output current is detected while output currents are detected from other sensors is excluded from the measurement system (electrically disconnected, the measured value of the output current not used with the electric connection unchanged, etc.).

Figure 16A:
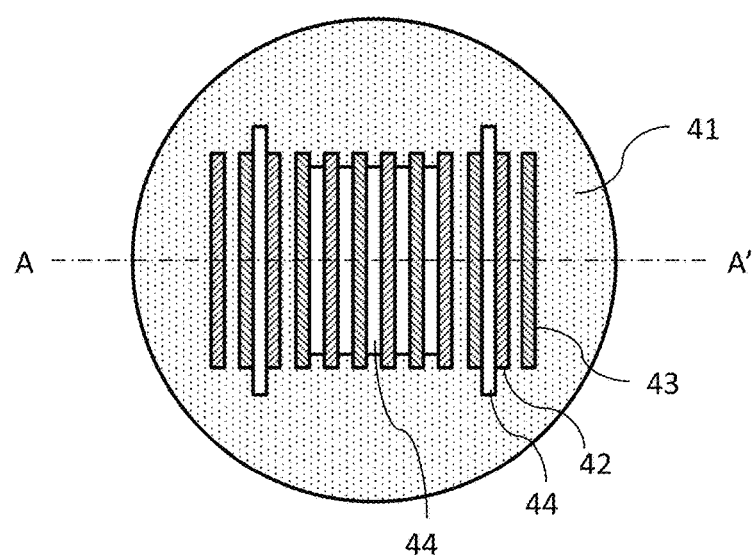
FIG. 16(a) is a schematic diagram according to one embodiment of a dryness/wetness responsive sensor.
Figure 16B:
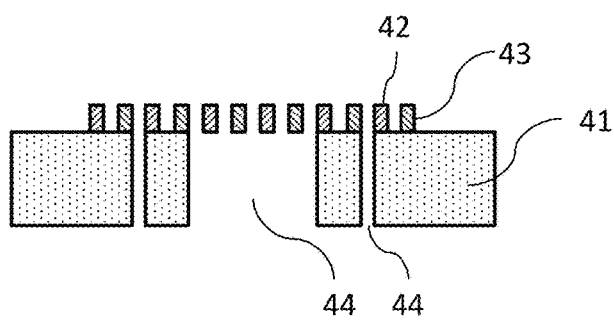
FIG. 16(b) is an A-A' cross-section of the embodiment of FIG. 16(a).

As another modified embodiment of the sensor according to the present application, for example, while a substrate to which a metal is not attached is present in the gap between the cathode electrode and the anode electrode in the sensor structure described above, by removing the substrate of the gap portion through etching or the like, the air may be configured to be allowed to flow between the cathode electrode and the anode electrode while water is not attached to the sensor. More specifically, for example, by removing at least a part of positions corresponding to the gap between the thin wires as illustrated in FIG. 16, an opening portion passing through the front and rear sides of the substrate can be arranged. By configuring as such, the sensor can be used as a sensor for moisture contained in the air or any other component. In addition, by completely removing the substrate of the gap portion, in a case where the mechanical strength is decreased or in a case where an eigenfrequency is included for which there is a risk of the occurrence of a trouble according to resonance with a mechanical vibration applied from the outside under a use environment, a countermeasure such as configuring the substrate of a part of the gap portion to remain or the like may be established.

While the sensor described until now is assumed to be directly installed to the surface of a building such as a steel frame and have the use for evaluating the corrosion environment of the surface of the building, a use for evaluating not the environment of the surface but the corrosion environment of a free space may be considered. Also in the case of such a use, the sensor needs to be fixed inside a space. However, for such a reason, in a case where the sensor is directly attached to the surface of a certain large installation target object, there are cases where a substance attached to the object flows on the sensor in accordance with rain or the like, or splash jumps into the sensor, or there are cases where an airflow is different from that of the case of a free space, and accordingly, there are cases where there is an influence of the object on a measured value. In order to exclude such an adverse effect, it is preferable to employ a configuration in which the sensor is raised to a position located far from an installation position of an installation target object. More specifically, for example, one end of an attachment tool having a plate shape, a rod shape, or the like to which the sensor is attached is attached to an installation target object for installation, and one or a plurality of sensors may be attached at a position separate from the installation target object on an attachment member.

Figure 17:
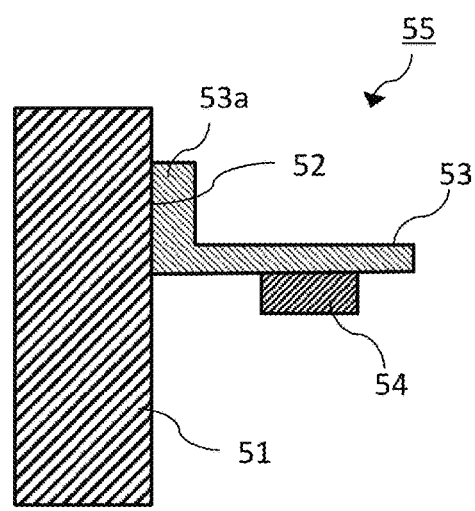
FIG. 17 is a schematic diagram according to one embodiment of a dryness/wetness responsive sensor assembly for remote installation.

In yet another embodiment, a dryness/wetness responsive sensor assembly for remote installation as illustrated in FIG. 17 can be provided, which comprises an attachment member with an attachment portion at one end for attachment to an object to which the dryness/wetness responsive sensor is attached so as to allow the dryness/wetness responsive sensor to be remotely located.

In addition, the dryness/wetness responsive sensor according to the present invention can be used as a humidity sensor. As described above, the size of the dryness/wetness responsive sensor according to the present invention can be decreased by significantly decreasing the inter-electrode distance to be less than that of a conventional sensor, and external power for driving the sensor is unnecessary. Accordingly, in addition to the improvement of the measurement accuracy as a humidity sensor, the dryness/wetness responsive sensor according to the present invention is expected to be able to manage a desired humidity condition also for an electronic apparatus, a physical distribution system, an industrial plant, and the like in which, conventionally, it is difficult to install the sensor due to a large size, no securement of external power, or the like.

EXAMPLES

Hereinafter, an embodiment will be described in which a dryness/wetness responsive sensor of which the sensitivity per unit area of the sensor area is improved by employing a simple structure by arranging two electrodes in a comb shape. It is understood that the present invention is not limited to such a specific form, and it should be noted that the technical scope of the present invention is defined by claims.

Figure 6:
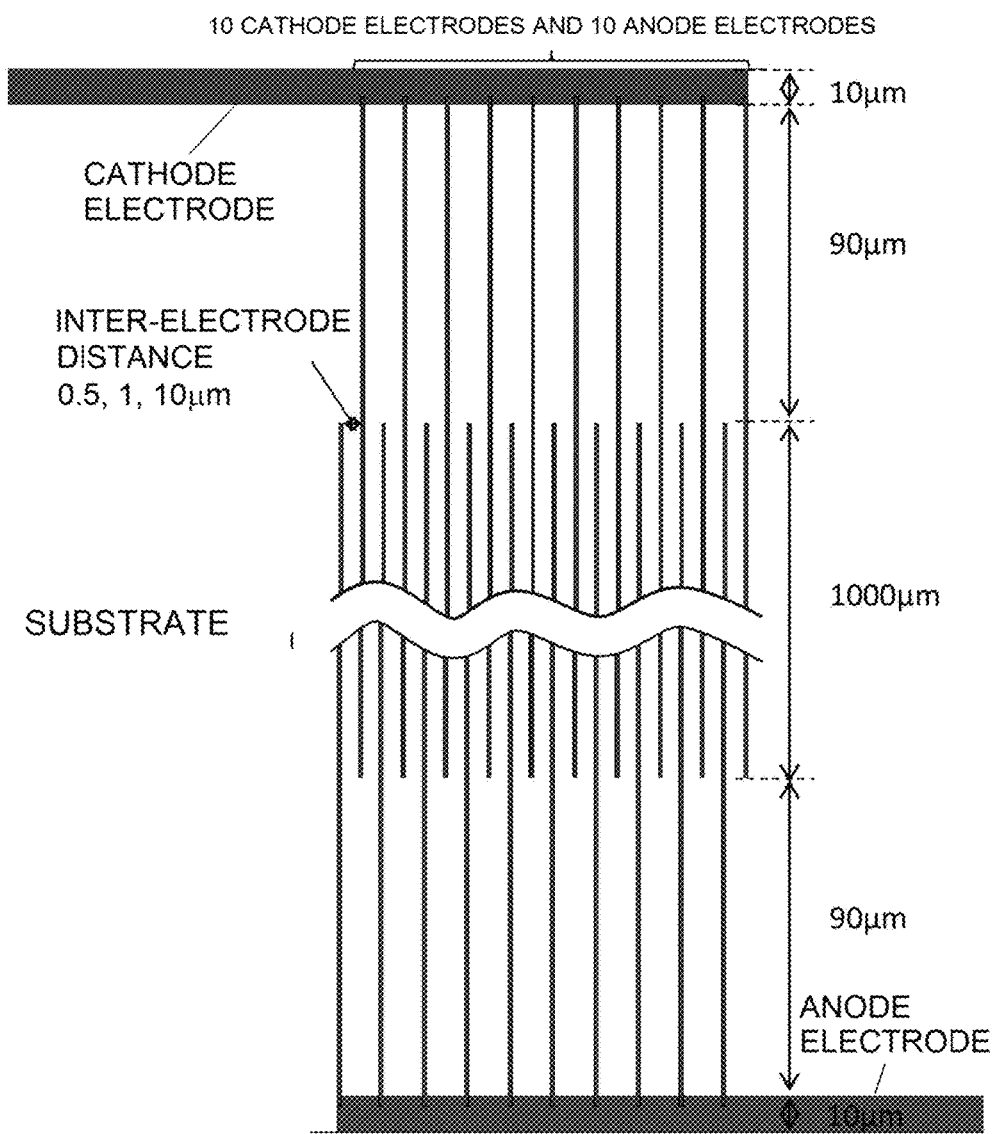
FIG. 6 is a diagram that illustrates an example of an electrode arrangement structure of a dryness/wetness responsive sensor based on detection of a galvanic current according to the present invention.

FIG. 6 illustrates the embodiment of a structure of the major portion, in other words, an electrode arrangement structure of the dryness/wetness responsive sensor in which an anode electrode of a metal such as iron and a cathode electrode of a metal different from the above-described metal such as silver are arranged in a comb shape on an insulating substrate. As the insulating substrate, for example, a silicon wafer having a silicon oxide film can be used. As examples of a material that can be used for the cathode electrode include gold, platinum, silver, titanium, and an alloy thereof; and carbon and allotrope thereof. For the anode electrode, for example, silver, copper, iron, zinc, nickel, cobalt, aluminum, tin, chromium, molybdenum, manganese, magnesium, or an alloy thereof can be used. However, in a case where silver and an alloy thereof are used for the anode electrode, for the cathode electrode, a material other than silver and the alloy thereof among the above-described materials of the cathode electrode may be used.

In each of the cathode electrode and the anode electrode, while a side close to a signal lead terminal (not illustrated in the drawing) of the dryness/wetness responsive sensor for the outside is unified as one to be a concentrated portion (the upper and lower sides in FIG. 6 are denoted by thick lines running in the horizontal direction), the concentrated portion branches into a plurality of parts near each terminal end portion. In the embodiment illustrated in FIG. 6, ten branches of each electrode are disposed. The branching cathode electrodes and the branching anode electrodes extend in a parallel direction (more specifically, an antiparallel direction; hereinafter, simply referred to as a parallel direction) and, for most of the extended distance, run parallel in the parallel direction with approaching each other. In this embodiment, the concentrated portions of the cathode electrode and the anode electrode extend in the antiparallel direction with being separate by 1180 µm, and each branching portion extends by 1090 µm toward an opposing concentrated portion. Each thin wire of the branching portion runs parallel in a direction parallel to the thin wire of the extended portion of the opposite side over 1000 µm except for 90 µm of the root portion. As a gap (a separation distance between the branching thin wire of the cathode electrode and the branching thin wire of the anode electrode) between both the electrodes of this parallel running portion, in this embodiment, three distances of 0.5 µm, 1 µm, and 10 µm were produced. In this embodiment, ten branching thin wires of the cathode electrode and ten branching thin wires of the anode electrode run parallel over 1000 µm. Since there are 19 parallel running sites (gaps between the branching thin wires of the cathode electrode and the anode electrode) between the branching thin wires, a total parallel running distance is 1000 µm×19=19 mm. Since a structure in which the inter-electrode distance is significantly decreased to be less than about 20 µm that is a conventional practical limit can be manufactured easily and stably, according to the present invention, a very narrow inter-electrode distance and a long running distance can be realized inside a small sensor area, and accordingly, the sensitivity per unit area in the sensor area can be significantly improved.

Figure 7A:
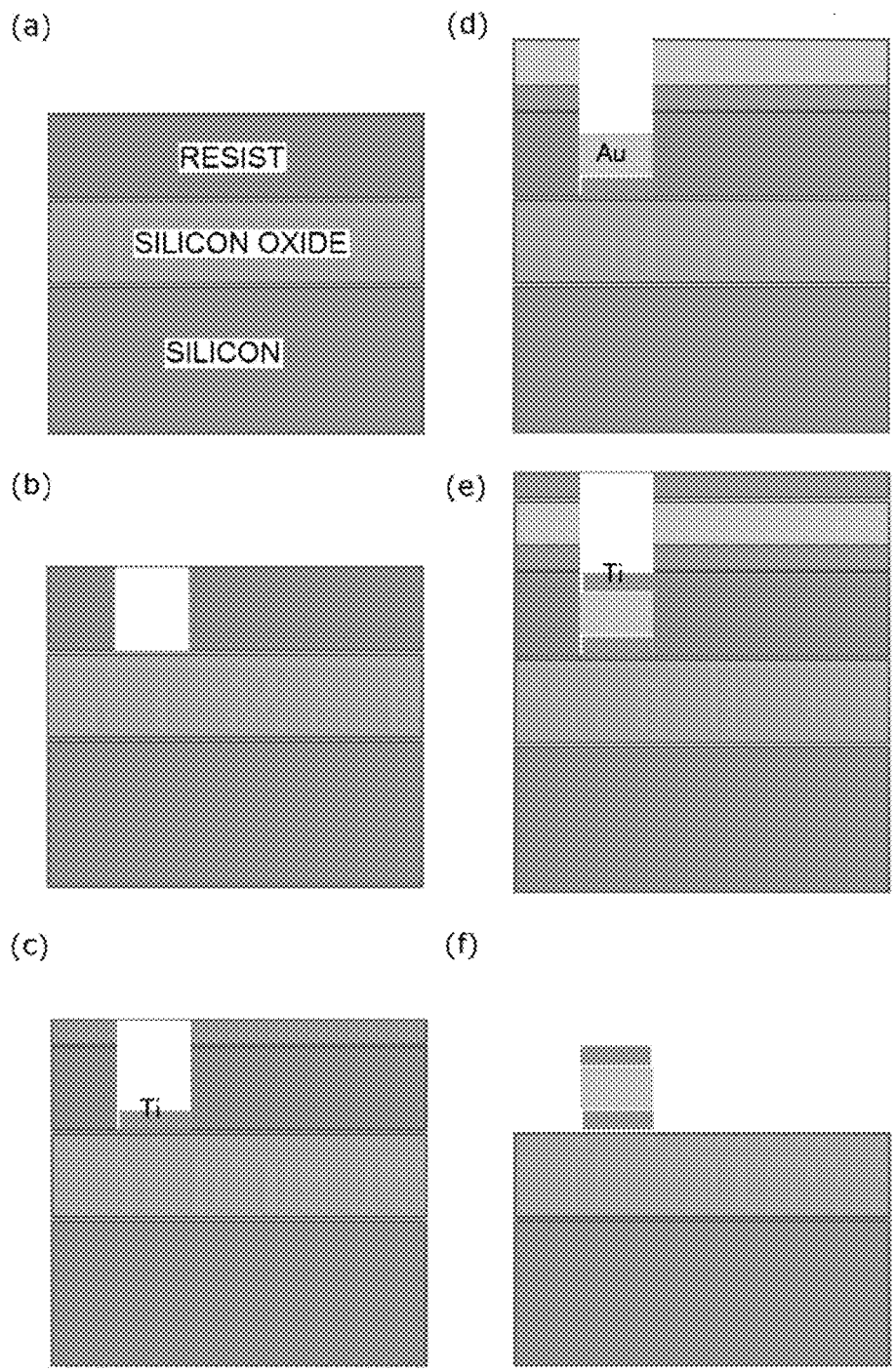
FIG. 7A is a diagram for schematically illustrating the former half of the manufacturing process of the dryness/wetness responsive sensor of an embodiment of the present invention.
Figure 7B:
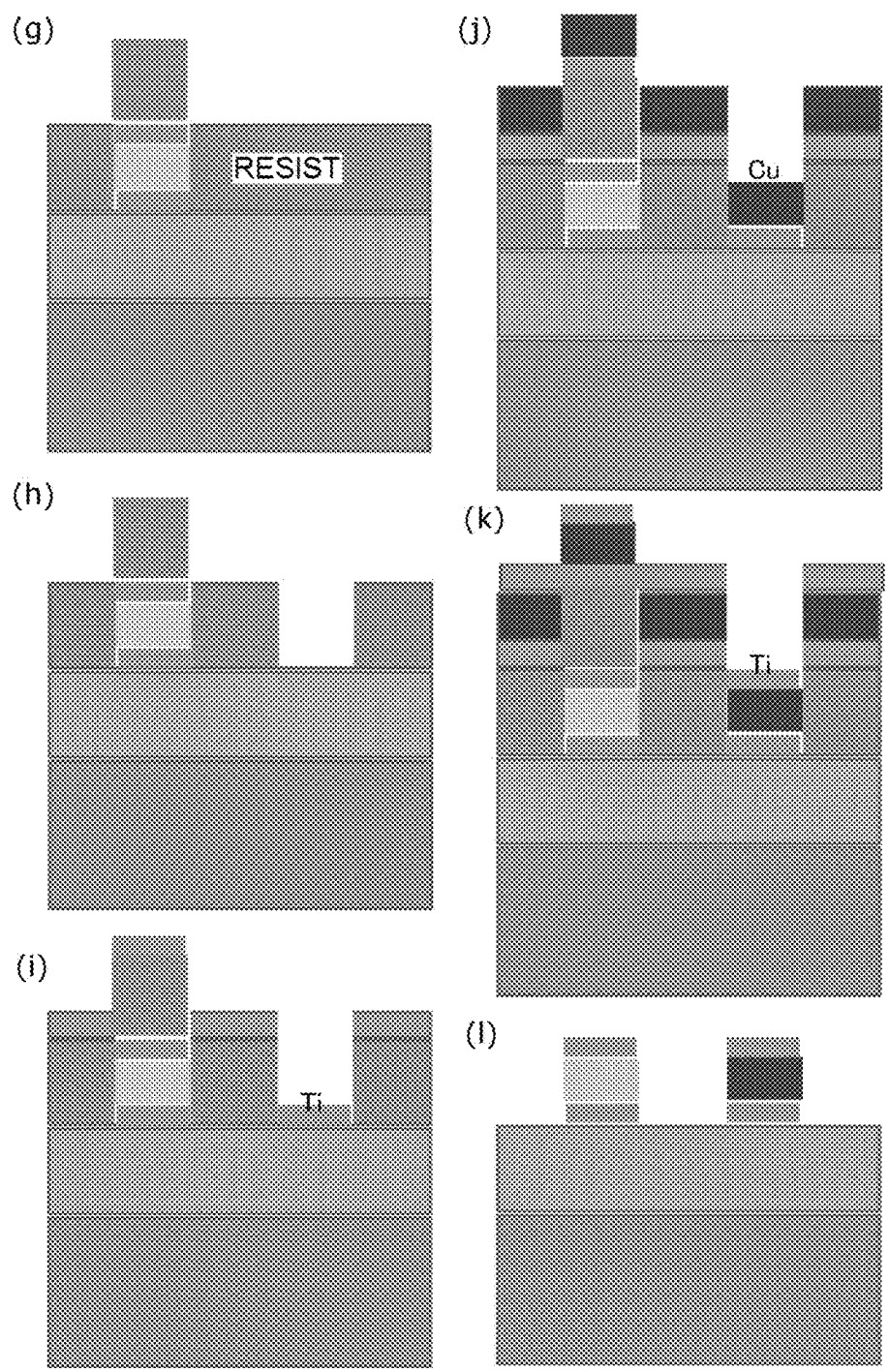
FIG. 7B is a diagram for schematically illustrating the latter half of a process of manufacturing the dryness/wetness responsive sensor of the embodiment of the present invention.

FIGS. 7A and 7B illustrate an example of the process configured by Steps (a) to (I) performed for generating a dryness/wetness responsive sensor having the structure illustrated in FIG. 6. FIGS. 7A and 7B correspond to a portion of the sensor in which thin wires of the cathode electrode and the anode electrode run parallel. A silicon wafer having a silicon oxide film on the surface was prepared, the surface thereof is coated with a resist (Step (a)), and a resist located at a position at which a cathode electrode is to be disposed was removed through photolithography (Step (b)). Next, by depositing titanium of 10 nm on the whole, an adhesive layer used for the cathode electrode was formed at the position at which the resist was removed (Step (c)). In addition, gold of 150 nm was deposited on the whole (Step (d)), and, next, titanium of 10 nm was deposited (Step (e)), whereby a main body of the cathode electrode formed from gold was formed at this position, and a stabilization layer formed from titanium was formed thereon. In this way, since the formation of the cathode electrode was completed, by lifting off the resist and the remaining metal layer, only the cathode electrode was caused to remain on a silicon oxide layer (Step (f)). Next, by performing a series of steps (Steps (g) to (I): here, a layer to be deposited as a metal of the main body of the anode electrode in Step (j) is a layer of copper having a thickness of 150 nm) similar to that of the cathode electrode, an anode electrode was formed at a position running parallel with the cathode electrode.

Figure 8A:
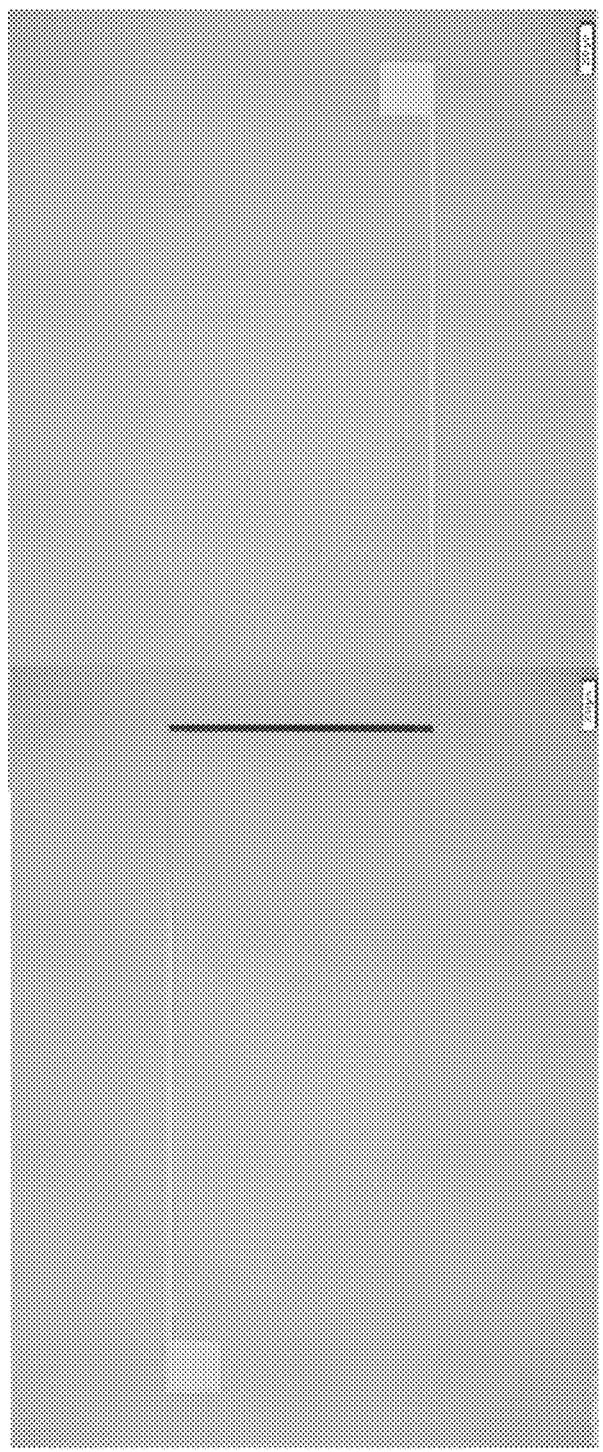
FIG. 8A is a photograph of the whole of the cathode and anode electrodes of the dryness/wetness responsive sensor of the embodiment of the present invention.

The whole electrode portion of the dryness/wetness responsive sensor manufactured in this way is illustrated in FIG. 8A. When FIG. 8A is seen with being positioned in a horizontally long direction, near an upper left corner and a lower right corner, electrode pads (signal lead terminal) connecting lead wires toward the cathode electrode and the anode electrode are seen as square areas of a color thinner than that of the periphery. Wires (portions of a color that is slightly thinner than that of the periphery) horizontally running from the electrode pads are concentrated portions horizontally running near the upper end and the lower end in FIG. 6. A black linear shaped portion vertically running at the center in FIG. 8A represents the branching portions of the cathode electrode and the anode electrode vertically running near the center in FIG. 6. A photograph acquired by enlarging a portion near the center of this branching portion illustrated in FIG. 8A is illustrated in FIG. 8B. As described above, since three kinds of dryness/wetness responsive sensors having inter-electrode distances of 10 µm, 1 µm, and 0.5 µm are produced, enlarged photographs of branching portions of these three kinds are illustrated in FIG. 8B. In order to evaluate the basic performance of the dryness/wetness responsive sensor, in any one of these three kinds of sensors, 10 thin wires of branching portions of each of the cathode electrodes and the anode electrodes are prepared. In a case where an actual dryness/wetness responsive sensor is configured, in order to effectively use the area of the main portion of the sensor that can be used, for covering the whole area of the main body or almost the whole area with the thin wires of the branching portions, as the inter-electrode distance is decreased, the number of the thinned lines increases. Accordingly, by decreasing the inter-electrode distance, it should be noted that, based on both an effect of an increase in the sensitivity per unit parallel running distance in accordance with the decrease in the inter-electrode distance and an effect of an increase in the parallel running distance per unit area, the sensitivity of this sensor is remarkably increased.

Figure 9A:
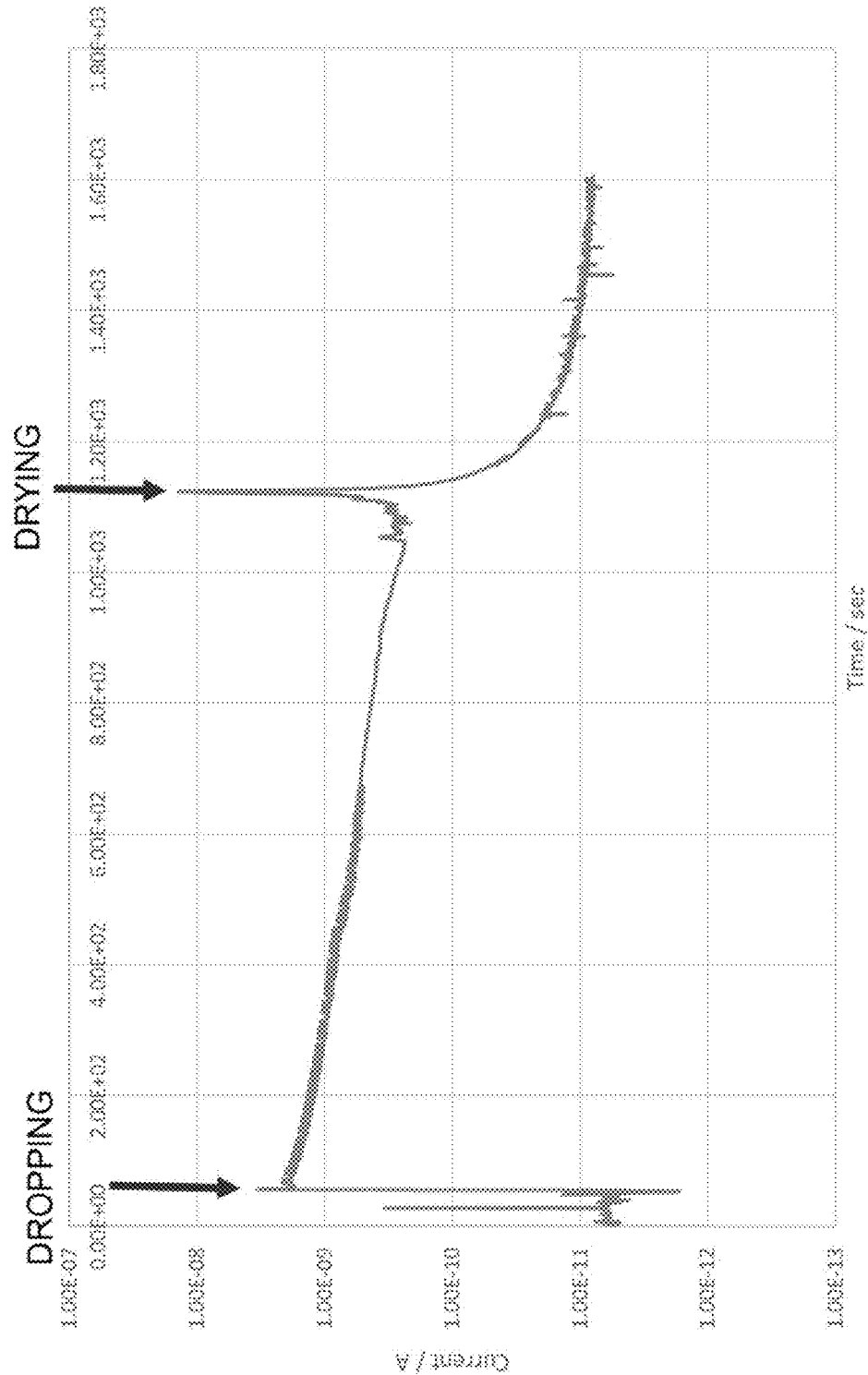
FIG. 9A is a diagram for illustrating a temporal change of the output of the dryness/wetness responsive sensor according to the present invention.

By dropping down water to the dryness/wetness responsive sensor produced in this way and measuring a change in the flowing current, the sensitivity of the dryness/wetness responsive sensor according to the present invention was actually measured. Actually-measured data for the dryness/wetness responsive sensors having inter-electrode distances of 10 µm, 1 µm, and 0.5 µm are illustrated in FIG. 9B.

In the measurement, pure water of 1 µL was dropped onto the concentrated portion of the dryness/wetness responsive sensor illustrated in FIG. 6, in other words, the comb-shaped electrode portion, and the sensor was dried, and a time elapse of the current for a while was measured. As can be understood from a graph illustrating a temporal change of the output of the dryness/wetness responsive sensor illustrated in FIG. 9A, when the water film immediately after the dropping is thick, the dissolved amount of the metal (here, copper that is the component of the anode electrode) depends on the amount of water, and accordingly, as the amount of water is increased, the corrosion speed becomes higher, and the output of the sensor becomes larger. As time passes, the water film becomes thin and narrow, the corrosion speed decreases, and the output of the sensor also decreases. Immediately before the sensor is dried, the water film becomes very thin, and accordingly, oxygen can easily arrive at the surface of the gold electrode, and oppositely, the corrosion speed increases. When the sensor is dried, in accordance with a decrease in moisture remaining so as to cause the electrodes to be in contact, resistance between the electrodes increases, and accordingly, the current decreases.

When an average value of the current changing in this way from dropping liquid droplets onto the sensor until immediately before the sensor is dried is taken, the average value is about 400 pA in a case where the inter-electrode distance is a width of 10 µm and is about 800 pA in the case of the inter-electrode distance is a width of 1 µm or 0.5 µm, and the improvement of the output value in accordance with a decrease in the width up to 1 µm could be confirmed. In this embodiment, while gold and copper are used as the metal materials of the electrodes, it is understood that the output (current) of the sensor depends on a combination of the metal materials of the electrodes. For example, comparing combination of Ag/Fe with that of Au/Ag, the combination of Ag/Fe has a higher corrosion speed per the same unit area, and accordingly, the acquired current value is larger. Instead of that, since Au/Ag has less consumption of electrodes and has a longer life.

As described above, in the embodiment illustrated in FIG. 6, while the number of each of the cathode electrodes and the anode electrodes is 10, considering to lay electrodes as possibly as can between a certain length (range), the laying density of the electrodes can be estimated as below. When the width of the electrode itself is 1 µm, and the number of pairs of electrodes is n, in an inter-electrode distance of 10 µm, the laying width is calculated as 2n+10× (2n−1)=22n−10 µm. Similarly, in the inter-electrode distances of 1 µm and 0.5 µm, the laying widths are respectively 4n−1 µm and 3n−0.5 µm. Accordingly, when the inter-electrode distance of 10 µm is used as the reference, the ratio of the number of pairs to the same laying width for 1 µm is (22n−10)/(4n−1)=(22−10/n)/(4−1/n) and, when n is sufficiently large (for example, 100 or more), a fraction having the denominator of n can be regarded as zero, and thus, 22/4=5.5. For 0.5 µm, the value of this ratio is 22/3=7 through similar calculation. In consideration of the average value of the current acquired in the embodiment, for the same laying width, when the inter-electrode distance of 10 µm is changed to 1 µm and 0.5 µm, we can say the output becomes 11 times and 14 times as large, respectively. Since the S/N ratio of 1:100 or more is obtained even for the conventional measurement system, we can say that the experimentally produced sensor of the above embodiment can also perform the sensing without amplification or noise filtering. When the width of the electrode itself is configured to be narrower (thinner), the number of pairs for the same laying width is increased, allowing the output to be further improved.

Figure 10:
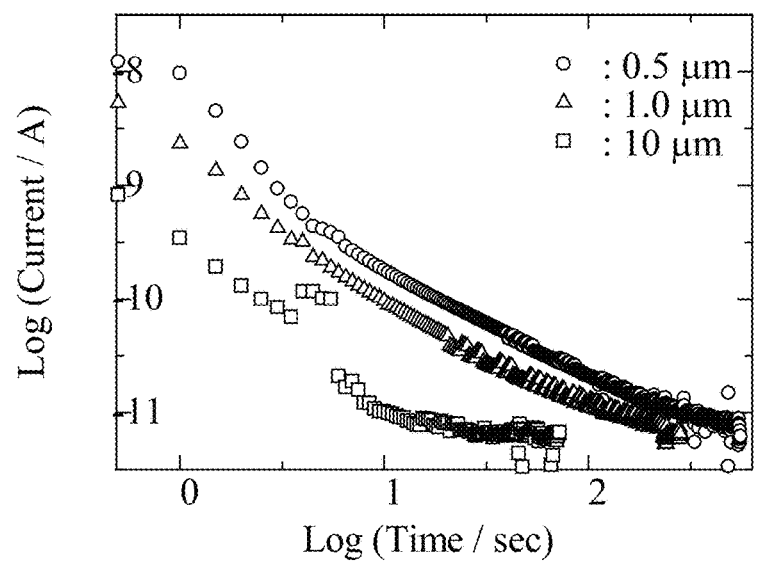
FIG. 10 is a diagram for illustrating the attenuation curves of the current values after recording the maximum current value in the dryness/wetness responsive sensors of the embodiment of the present invention having inter-electrode distances of 10 µm, 1 µm, and 0.5 µm.

In relation to FIG. 9B, FIG. 10 represents attenuation curves of current values after recording a maximum current value in dryness/wetness responsive sensors of the present embodiment with the inter-electrode distance of 10 µm, 1 µm, and 0.5 µm. As can be understood from FIG. 10, the time the current reaches the background current ($10^{-11}$ A) becomes longer as the inter-electrode distance is reduced. This suggests that the current can be measured until the size of liquid droplets remaining between the electrodes is reduced to a smaller size, as the inter-electrode distance is decreased. In other words, it is suggested that the dryness/wetness responsive sensor according to the present invention can determine the size of liquid droplets remaining between the electrodes.

Figure 11:
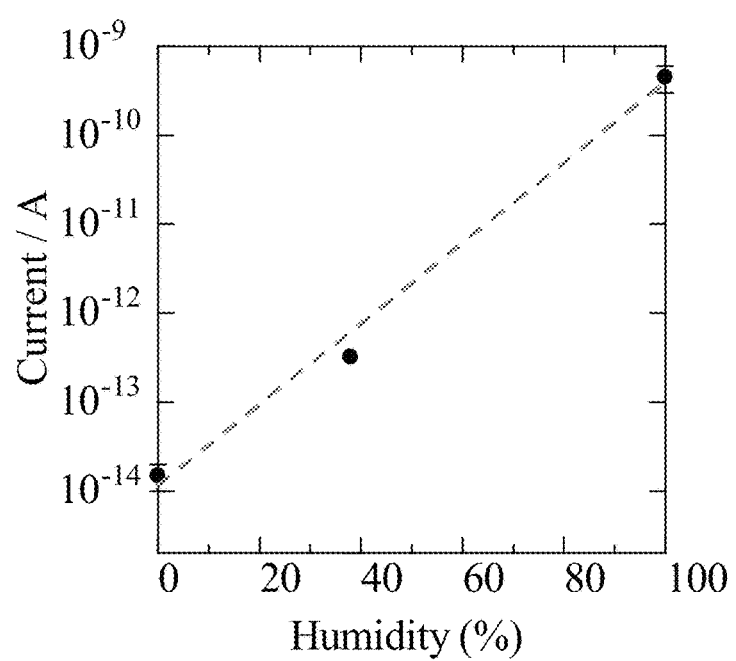
FIG. 11 is a diagram for illustrating the results of output currents measured under humidity conditions of 0% RH, 38% RH, and 100% RH by using the dryness/wetness responsive sensor of the embodiment of the present invention having the inter-electrode distance configured to be 1.0 µm.

FIG. 11 is a result of output currents measured under humidity conditions of 0% RH, 38% RH, and 100% RH by using the dryness/wetness responsive sensor of the present embodiment having an inter-electrode distance of 1.0 µm. As can be understood from FIG. 11, the dryness/wetness responsive sensor according to the present invention can perform high-precision detection in the humidity range of 0 to 100% RH. Each humidity condition is set as below.

0% RH: a state in which the surface of the sensor is dried using a drier

Figure 12:
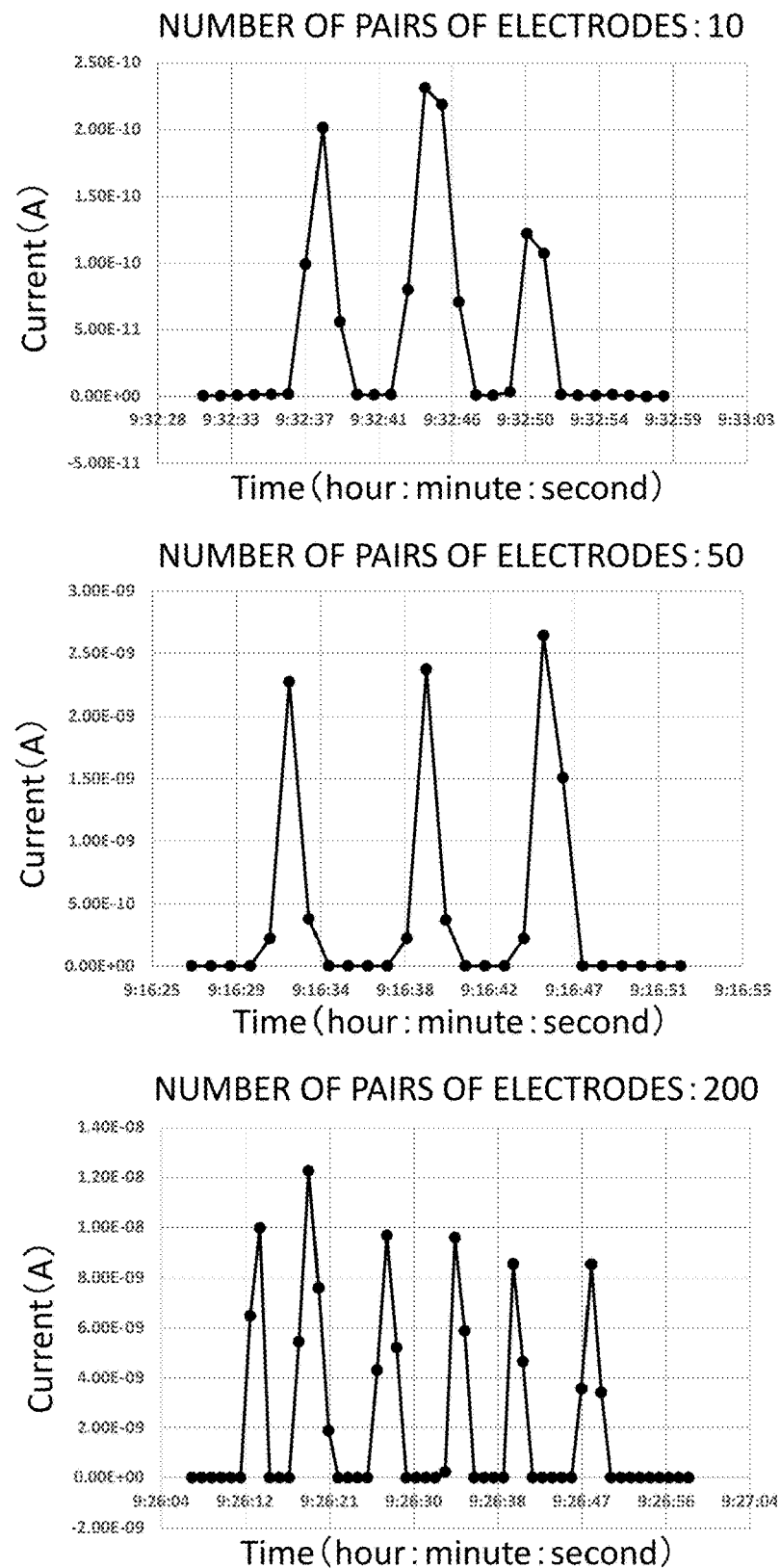
FIG. 12 is a diagram for illustrating examples of the output of the dryness/wetness responsive sensor of the embodiment of the present invention having an inter-electrode distance of 1.0 µm and the number of pairs of electrodes of 10, 50 and 200.

38% RH: a value acquired by measuring the humidity of the measurement environment using a commercially available hygrometer 100% RH: a state in which the entire surface of the sensor is cloudy by blowing out a breath onto the surface of the sensor Next, by using a production method similar to the method described above, three kinds of dryness/wetness responsive sensors having an inter-electrode distance of 1.0 m and the number n of pairs of electrodes of 10, 50, and 200 were produced, and the sensitivity of each of the sensors was actually measured. The result is illustrated in FIG. 12.

In the measurement, a breath is blown out to the surface of the sensor (the current value increases in accordance therewith), and, after the current value is returned to the background, an operation of blowing out a breath is repeated again. As can be understood from FIG. 12, by increasing the number n of pairs of electrodes from 10 to 50 and 200, the output of the sensor was increased respectively to 20 times and 50 times. In this way, in the dryness/wetness responsive sensor according to the present invention, by adjusting the number of sets of electrodes in accordance with the laying condition and the like in addition to the inter-electrode distance, the output of the sensor can be improved.

In the dryness/wetness responsive sensor, when a galvanic current flows repeatedly, the metal of the anode electrode is ionized, and accordingly, the anode electrode is gradually consumed. In addition, in a case where a long-term use under an environment having high humidity and a large salt damage is assumed, particularly, in a dryness/wetness responsive sensor having thin electrodes for increasing the laying density, there is a possibility that the inter-electrode distance is gradually increased or the thin wire of the electrode is cut out in accordance with the consumption of the anode electrode. In order to address these problems with the laying density of the electrodes maintained, for example, the thickness of the anode electrode may be increased, or the width of the anode electrode may be increased instead of the width of the cathode electrode may be decreased. In a case where the inter-electrode distance is very short, the influence of a slight increase in the inter-electrode distance according to the consumption of the anode electrode on a result of the measurement increases. In a case where such an influence matters, for example, by using a principle that the consumption of the metal of the anode electrode is in proportion to the time integral of a galvanic current, a countermeasure of performing compensation calculation for the result of the measurement as the whole measurement system may be established.

Though the present embodiment shows an example in which the inter-electrode distance is constant, the sensor system may combine a plurality of sensor modules having different inter-electrode distances according to a desired application or the like.

INDUSTRIAL APPLICABILITY

As described above, according to the present invention, a dryness/wetness responsive sensor having a size significantly smaller than that of a conventional case without decreasing the sensitivity is provided and thus can be installed to various places without being conspicuous, and contributions thereof to the improvement of the accuracy of the evaluation or the prediction of corrosion and degradation of a structure such as a steel frame exposed to an corrosive environment are expected. In addition, the dryness/wetness responsive sensor according to the present invention can be applied not only to corrosive environment monitoring but also to various humidity measurements such as a dryness/wetness monitoring/tracking until physical distribution from manufacturing/growing industrial products, foods, and the like, a mold generation status prediction for an indoor bathroom, a washer, or the like.

CITATION LIST

Non Patent Literature

Non Patent Literature 1: F. Mansfeld at al., Corrosion Science, Vol. 16, pp. 111' to 122 (1976)

Non Patent Literature 2: Peter Norberg, Service Life Prediction Methodology and Metrologies, ACS Symposium Series 805, Jonathan W Martin and David R. Bauer, Eds., American Chemical Society, 2002, pp 23-36

Non Patent Literature 3: T. Shinohara et al., Journal of Metals, Materials and Minerals, Vol. 20 No. 2 pp. 23-27, 2010

Non Patent Literature 4: Shinohara. Tadashi, etc. Materials and Environments Vol. 54, No. 8 (2005) pp. 375-382

Non Patent Literature 5: Engaji et al, Toyota Tech. rep., 40 (1987) p. 57

IN THE FIGURES

11: Thin wire of first metal;
12: Thin wire of second metal;
13: Cathode electrode;
14: Anode electrode;
21: Insulating substrate;
22: Thin wire of first metal;
23: Thin wire of second metal;
24: Insulating protection film;
25: Opening;
26: Meshed member;
31: Insulating substrate;
32: Thin wire of first metal;
33: Thin wire of second metal;
34: Opening (Groove-shaped opening);
35: Insulating protection film;
41: Insulating substrate;
42: Thin wire of first metal;
43: Thin wire of second metal;
44: Opening;
51: Installation target object;
52: Attachment face;
53: Attachment member;
53a: Attachment portion;
54: Dryness/wetness responsive sensor; and
55: Dryness/wetness responsive sensor assembly for remote installation

The invention claimed is:

1. A dryness/wetness responsive sensor comprising
a thin wire of a first metal,
a thin wire of a second metal, the second metal being different from the first metal,
wherein the thin wire of the first metal and the thin wire of the second metal are disposed in juxtaposition with each other on an insulating substrate, and wherein a spacing between the first thin wire and the second thin wire is in a range of 5 nm or more and less than 20 μm, a current measurement means electrically connected to the thin wire of the first metal and the thin wire of the second metal, and an insulating protection film covering an area in which the thin wire of the first metal and the thin wire of the second metal are disposed in juxtaposition with each other, wherein the insulating protection film has a groove-shaped opening that exposes at least a part of the thin wires.

2. The dryness/wetness responsive sensor according to claim 1, wherein the groove-shape opening further exposes at least a part of a gap between the thin wire of the first metal and the thin wire of the second metal.

3. The dryness/wetness responsive sensor according to claim 1, comprising a plurality of at least one selected from the group consisting of the thin wire of the first metal and the thin wire of the second metal, wherein the thin wire of the first metal extends from a first side towards a second side that is opposite to the first side and the thin wire of the second metal extends from the second side towards the first side such that the thin wire of the first metal and the thin wire of the second metal run in parallel.

4. The dryness/wetness responsive sensor according to claim 1, wherein the thin wire of the first metal and the thin wire of the second metal are arranged in a double spiral.

5. The dryness/wetness responsive sensor according to claim 1, wherein the insulating substrate is a silicon substrate with a silicon oxide film on its surface.

6. The dryness/wetness responsive sensor according to claim 1, wherein the first metal is selected from a group consisting of gold, platinum, silver, titanium, an alloy thereof, and carbon.

7. The dryness/wetness responsive sensor according to claim 1, wherein the second metal is selected from a group consisting of silver, copper, iron, zinc, nickel, cobalt, aluminum, tin, chromium, molybdenum, manganese, magnesium, and an alloy thereof.

8. The dryness/wetness responsive sensor according to claim 1, wherein a number of pairs of the thin wire of the first metal and the thin wire of the second metal is more than 50.

9. The dryness/wetness responsive sensor according to claim 1, further comprising a meshed member covering an area in which the thin wire of the first metal and the thin wire of the second metal are disposed in juxtaposition with each other.

10. A dryness/wetness responsive sensor assembly for remote installation comprising the dryness/wetness responsive sensor according to claim 1 attached to an attachment member having an attachment portion at one end for attachment to an object such that the dryness/wetness responsive sensor is attached to the object via the attachment member.

11. A dryness/wetness responsive sensor comprising
a thin wire of a first metal,
a thin wire of a second metal, the second metal being different from the first metal, and
a current measurement means electrically connected to the thin wire of the first metal and the thin wire of the second metal, wherein the thin wire of the first metal and the thin wire of the second metal are disposed in juxtaposition with each other on an insulating substrate, wherein a spacing between the first thin wire and the second thin wire is in a range of 5 nm or more and less than 20 μm, and wherein the insulating substrate comprises an opening portion passing through from one side to an opposite side of the insulating substrate, and the opening portion is obtained by removing at least a part of the insulating substrate corresponding to the spacing between the thin wire of the first metal and the thin wire of the second metal.

12. The dryness/wetness responsive sensor according to claim 11, comprising a plurality of at least one selected from the group consisting of the thin wire of the first metal and the thin wire of the second metal, wherein the thin wire of the first metal extends from a first side towards a second side that is opposite to the first side and the thin wire of the second metal extends from the second side towards the first side such that the thin wire of the first metal and the thin wire of the second metal run in parallel.

13. The dryness/wetness responsive sensor according to claim 11, wherein the thin wire of the first metal and the thin wire of the second metal are arranged in a double spiral.

14. The dryness/wetness responsive sensor according to claim 11, wherein the insulating substrate is a silicon substrate with a silicon oxide film on its surface.

15. The dryness/wetness responsive sensor according to claim 11, wherein the first metal is selected from a group consisting of gold, platinum, silver, titanium, an alloy thereof, and carbon.

16. The dryness/wetness responsive sensor according to claim 11, wherein the second metal is selected from a group consisting of silver, copper, iron, zinc, nickel, cobalt, aluminum, tin, chromium, molybdenum, manganese, magnesium, and an alloy thereof.

17. The dryness/wetness responsive sensor according to claim 11, wherein a number of pairs of the thin wire of the first metal and the thin wire of the second metal is more than 50.

18. The dryness/wetness responsive sensor according to claim 11, further comprising a meshed member covering an area in which the thin wire of the first metal and the thin wire of the second metal are disposed in juxtaposition with each other.

19. A dryness/wetness responsive sensor assembly for remote installation comprising the dryness/wetness responsive sensor according to claim 11 attached to an attachment member having an attachment portion at one end for attachment to an object such that the dryness/wetness responsive sensor is attached to the object via the attachment member.

* * * * *